US008889114B2

(12) United States Patent
Lopes et al.

(10) Patent No.: US 8,889,114 B2
(45) Date of Patent: Nov. 18, 2014

(54) COMPOSITION AND METHOD FOR THE INHIBITION OF POSTOPERATIVE ADHESIONS SEVERITY

(75) Inventors: Jackson Brandão Lopes, Ipatinga (BR); Luis Alberto Oliveira Dallan, Sao Paulo (BR)

(73) Assignees: Jackson Brandao Lopes, Ipatinga-MG (BR); Luis Alberto Oliveira Dallan, Sao Paulo-SP (BR); Fundacao Sao Francisco Xavier, Ipatinga-MG (BR)

( * ) Notice: Subject to any disclaimer, the term of this patent is extended or adjusted under 35 U.S.C. 154(b) by 769 days.

(21) Appl. No.: 12/934,634

(22) PCT Filed: Mar. 19, 2009

(86) PCT No.: PCT/BR2009/000075
§ 371 (c)(1),
(2), (4) Date: Sep. 24, 2010

(87) PCT Pub. No.: WO2009/117793
PCT Pub. Date: Oct. 1, 2009

(65) Prior Publication Data
US 2011/0165095 A1 Jul. 7, 2011

(30) Foreign Application Priority Data

Mar. 26, 2008 (BR) .................................... 0801422

(51) Int. Cl.
*A61P 9/08* (2006.01)
*A61P 17/02* (2006.01)
*A61K 38/18* (2006.01)
*A61K 31/722* (2006.01)

(52) U.S. Cl.
CPC ............... *A61K 38/18* (2013.01); *A61K 31/722* (2013.01); *A61K 38/1808* (2013.01); *A61K 38/1833* (2013.01); *A61K 38/1825* (2013.01)
USPC ..................... 424/78.06; 424/78.02; 424/400; 424/484; 514/9.1; 514/9.2; 514/18.6

(58) Field of Classification Search
None
See application file for complete search history.

(56) References Cited

U.S. PATENT DOCUMENTS

| 6,030,635 | A | 2/2000 | Gertzman et al. | |
|---|---|---|---|---|
| 6,124,273 | A * | 9/2000 | Drohan et al. | 514/55 |
| 7,265,097 | B2 | 9/2007 | Kydonieus et al. | |
| 2002/0010150 | A1 | 1/2002 | Cortese et al. | |
| 2003/0158302 | A1 * | 8/2003 | Chaput et al. | 524/115 |
| 2004/0001879 | A1 | 1/2004 | Guo et al. | |
| 2005/0019824 | A1 * | 1/2005 | Alderson et al. | 435/6 |
| 2005/0042251 | A1 * | 2/2005 | Zhang et al. | 424/423 |
| 2005/0214255 | A1 * | 9/2005 | Elson et al. | 424/85.7 |
| 2006/0258562 | A1 | 11/2006 | Tennenbaum | |

FOREIGN PATENT DOCUMENTS

| CA | 2079042 A1 | 3/1993 |
|---|---|---|
| CN | 101250498 A * | 8/2008 |
| EP | 1508344 A1 | 2/2005 |
| EP | 2274003 B1 | 11/2013 |
| WO | 91/18999 A1 | 12/1991 |
| WO | 96/35433 A1 | 11/1996 |
| WO | 2006/116559 A2 | 11/2006 |
| WO | 2007/124132 A2 | 11/2007 |

OTHER PUBLICATIONS

Chen et al. Method for culturing liver cell by hepatocyte-carrying growth factor polylactic acid-0-carboxymethyl shellglycan nanoparticles. English Abstract of CN101250498 A (Aug. 27, 2008).*
Lopes et al. Synergy between keratinocyte growth factor and carboxymethyl chitosan reduces pericardial adhesions. Ann. Thorac. Surg. vol. 90:566-572 (Aug. 2010).*
Fan Tingjun et al., "Establishment of a Novel Corneal Endothelial Cell Line from Domestic Rabbit, Oryctolagus Curiculus", Science in China Series C: Life Sciences, vol. 50, No. 2, Apr. 2007, pp. 161-169 XP002479772, ISSN: 1006-9305, Abstract.
Liu Hong-Jun et al., "Adenoiral-Mediated Gene Expression of Hepatocyte Growth Factor Prevents Postoperative Peritoneal Adhesion in a Rat Model", Surgery, vol. 140, No. 3, Sep. 2006, pp. 441-447, XP005610496, ISSN: 0039-6060, Abstract.
Tyrone J. Krause. et al., "Prevention of Pericardial Adhesions with N-O Carboxymethylchitosan in the Rabbit Model", Journal of Investigative Surgery: The Official Journal of the Academy of Surgical Research 2001, vol. 14, No. 2, Mar. 20001, pp. 93-97, XP009041568, ISSN: 0894-1939, Abstract.
Jackson B. Lopes et al., Keratinocyte Growth Factor: A New Mesothelial Targeted Therapy to Reduce Postoperative Pericardial Adhesions pp. 313-318, European Journal of Cardio—thoraic Surgery 35 (2009).
European Search Report for European Application No. 09725636.6 dated Mar. 23, 2012.
Jackson B. Lopes et al, "Synergism Between Keratinocyte Growth Factor and Carboxymethyl Chitosan Reduces Pericardial Adhesions", Ann Thorac Surg. Aug. 2010, vol. 90, No. 2, pp. 5556-5572.
Fernanda R. De Abreu et al., "Preparation and Characterization of Carboxymethylchitosan", Polimeros: Ciencia e Tecnologia, 2005, pp. 79-83, vol. 15(2), Brazil.
Ian Y. R. Adamson et al., "Proliferation of Rat Pleural Mesothelial Cells in Response to Hepatocyte and Keratinocyte Growth Factors", Am J Respir. Cell Mol. Biol., 2000, pp. 345-349, vol. 23, Canada.
Amanpour S. et al., "Long-Term Evaluation of Laser-Treated Silicone (LTS) Membrane as a Pericardial Substitute: In Vivo Study", Journal of Long-Term Effects of Medical Implants, 2005, pp. 347-354, vol. 15(4), New York.
Steven L. Bennett, PH.D. et al, "Next-Generation HydroGel Films as Tissue Sealants and Adhesion Barriers", J Card Surg, 2003, pp. 494-499, vol. 18, Mass. USA.

(Continued)

*Primary Examiner* — Elizabeth C Kemmerer
*Assistant Examiner* — Regina M Deberry
(74) *Attorney, Agent, or Firm* — Roberts Mlotkowski Safran and Cole, P.C.

(57) ABSTRACT

The present invention refers to the use of growth factors, which are effective on mesothelial cell proliferation, used in a sterilized carboxymethylchitosan pharmaceutical composition employed to reduce postoperative adhesions severity. The present invention also provides a method to inhibit postoperative adhesions severity.

9 Claims, 9 Drawing Sheets

(56) References Cited

OTHER PUBLICATIONS

Yen Chang, MD. et al., "Mesothelium Regeneration on Acellular Bovine Pericardia Loaded with an Angiogenic Agent (Ginsenoside Rg1) Successfully Reduces Postsurgical Pericardial Adhesions", The Journal of Thoracic and Cardiovascular Surgery, 2006, pp. 867-874, vol. 132(4), Taiwan.

D. A. Duncan, M.D. et al., "Prevention of Postoperative Pericardial Adhesions with Hydrophilic Polymer Solutions", Journal of Surgical Research, 1988, pp. 44-49, vol. 45, Florida, USA.

Noriyoshi Kajihara, M.D. et al, "Three-Layered Synthetic Pericardial Substitutes Reduce Postoperative Pericardial Adhesions", The Journal of Thoracic and Cardiovascular Surgery, 2005, pp. 18-24, vol. 129, Japan.

Tyrone J. Krause, M.D. et al., "Prevention of Pericardial Adhesions with N-O Carboxymethylchitosan in the Rabbit Model", Journal of Investigative Surgery, 2001, pp. 93-97, vol. 14, New Jersey, USA.

Mark Hendrikx, M.D., et al., "Evaluation of a Novel Synthetic Sealant for Inhibition of Cardiac Adhesions and Clinical Experience in Cardiac Surgery Procedures", The Heart Surgery Forum, 2001, pp. 204-210, vol. 4(3), California USA.

Kazunori Masuoka et al., "The Interaction of Chitosan with Fibroblast Growth Factor-2 and its Protection from Inactivation", Biomaterials, 2005, pp. 3277-3284, vol. 26, Japan.

Metwally Mostafa E et al., "Fluid and Pharmacological Agents for Adhesion Prevention After Gynaecological Surgery", Cochrane Database of Systematic Reviews, 2006, Library number CD001298, Lancashire.

John D. Mitchell, M.D. et al., "Prevention of Postoperative Pericardial Adhesions with a Hyaluronic Acid Coating Solution: Experimental Safety and Efficacy Studies", The Journal of Thoracic and Cardiovascular Surgery, 1994, pp. 1481-1488, vol. 107 (Issue 6), Mass. USA.

J. D. Mitchell et al., "Reduction in Experimental Pericardial Adhesions Using a Hyaluronic Acid Bioabsorbable Membrane", European Journal of Cardiothoracic Surgery, 1994, pp. 149-152, vol. 8, Mass. USA.

Murat Ozeren et al., "Consequences of PTFE Membrane Used for Prevention of Re-Entry Injuries in Rheumatic Valve Disease", Cardiovascular Surgery, 2002, pp. 489-493, vol. 10(5), Turkey.

Robert J. Robinson, M.D. et al., "Prevention of Pericardial Adhesions with Dextran 70", The Annals of Thoracic Surgery, 1984, pp. 488-490, vol. 37(6), USA.

Joseph E. Dos Santos et al., "Characterization of Commercial Chitosan from Different Suppliers", Polimeros, 2003, pp. 242-249, vol. 13(4), Brazil.

James M. Seeger, M.D. et al., "Prevention of Postoperative Pericardial Adhesions Using Tissue-Protective Solutions", Journal of Surgical Research, 1997, pp. 63-66, vol. 68, USA.

Hiroyuki Tsukihara, MD.D. et al., "Prevention of Postoperative Pericardial Adhesions with a Novel Regenerative Collagen Sheet", Ann Thorac Surg, 2006, pp. 650-657, vol. 81, Japan.

International Search Report for International Application No. PCT/BR2009/000075, Mar. 22, 2012.

Ian Y.R. Adamson et al., Proliferation of Rat Pleural Mesothelial Cells in Response to Hepatocyte and Keratinocyte Growth Factors, Am. J. Respir. Cell Mol. Biol. 2000; vol. 23, pp. 345-349.

Tiffany Derrick et al., Effect of Polyanions on the Structure and Stability of Repifermin, (Keratinocyte Growth Factor-2), Journal of Pharmaceutical Sciences, 2007; vol. 96 No. 4, pp. 761-776.

Eric Hsu et al., Enhanced Stability of Recombinant Keratinocyte Growth Factor by Mutagenesis, Protein Engineering, Design & Selection, 2006; vol. 19 No. 4, pp. 147-153.

Makoto Igarashi et al., Characterization of Recombinant Human Fibroblast Growth Factor (FGF)-10 Reveals Functional Similarities with Keratinocyte Growth Factor (FGF-7), The Journal of Biological Chemistry, May 22, 1998; vol. 273, No. 21, pp. 13230-13235.

Emilia Pierro et al., Influence of Growth Factors on Proliferation and Morphogenesis of Rabbit Ovarian Mesothelial Cells In Vitro, Biology of Reproduction, 1996; vol. 54, pp. 660-669.

Maria Enoi Dos Santos Miranda et al., Rheological Aspects of N-Carboxymethyl-Chitosan in Diluted Solutions, Alimentos e Nutricao (UNESP). UNESP—Araraquara SP, 2003; vol. 14 No. 2, pp. 141-147.

Steven J. Prestrelski, Binding of Heparin to Basic Fibroblast Growth Factor Induces a Conformational Change, Archives of Biochemistry and Biophysics; 1992; vol. 293 No. 2, pp. 314-319.

Janet M. Trowbridge, Dermatan Sulfate Binds and Potentiates Activity of Keratinocyte Growth Factor (FGF-7), The Journal of Biological Chemistry, 2002; vol. 277, pp. 42815-42820.

Willy Arung et al., "Pathophysiology and Prevention of Postoperative Peritoneal Adhesions", World Journal of Gastroenterology, Nov. 7, 2011, vol. 17 No. 41, pp. 4545-4533.

Alessandro Sannino et al., "Biodegradable Cellulose-based Hydrogels: Design and Applications", Materials 2009, vol. 2, pp. 353-373.

S. Hein., "Chitosan Composites for Biomedical Applications: Status, Challenges and Perspectives", Materials Science and Technology, 2008, vol. 24 No. 9, pp. 1053-1061.

M. Prabaharan, et al., "Preparation and Characterization of Poly(L-lactic acid)-Chitosan Hybrid Scaffolds with Drug Release Capability", Wiley InterScience, Oct. 4, 2006, pp. 427-434.

* cited by examiner

COMPOSITION AND METHOD FOR THE INHIBITION OF POSTOPERATIVE ADHESIONS SEVERITY

INVENTION FIELD

This present invention, in its broadest concept, refers to the use of a composition containing an effective growth factor to inhibit postoperative adhesions. The invention includes a method to treat and inhibit postoperative adhesions, as well.

THE INVENTION'S FUNDAMENTS

Pericardial adhesions are formed between the epicardium, the parietal pericardium, the pleura and the sternum, after surgical interventions done to the heart and great vessels. These pericardial adhesions make it more difficult for future surgical interventions and add more morbidity and mortality, too.

Nowadays, reoperations are frequent and represent between 10 and 20% of all cardiac surgeries. The reoperations represented 22.8% of heart valves operations between 1980 and 1999 at the Heart Institute of São Paulo University Medical School.

Adhesions make these reoperations procedures more dangerous and longer, and many times it leads to iatrogenic damage of serious consequences. Right ventricle, anterior interventricular artery and aorto-coronary vascular grafts injuries have been described in up to 6% of the cases. The mortality rate may reach up to 50% when the intraoperative injury causes massive hemorrhages or when there is an injury of the vascular grafts.

Besides the intraoperative inconvenients, the pericardial adhesions cause a right ventricle dysfunction and a reduction of the integrity of the aorto-coronary vascular grafts.

Adhesions are formed after a physical and/or chemical aggression of the pericardium's mesothelial cells layer, creating on it a nude and physiologically damaged surface. This favors the accumulation of fibrin, which creates connections between the damaged surfaces of the parietal and visceral membranes. These fibrin connections are called adhesive bands. With the tissue repair process, these adhesive bands suffer infiltration of fibroblasts, which perform the deposition of collagens fibers replacing the fibrin, and the neovascularization is developed. This process results in firm and of difficult manipulation adhesions.

The most common place to do studies regarding postoperative adhesions prevention is the peritoneum. Most of the concepts have been initially tested in the peritoneal cavity due to the simple approach of this cavity and the possibility of using small animals like rats for experiments. Many theories started and finished in these cavities. Comparatively, very few have been tested in the pericardium and the pleura.

Many methods have been tested to try to reduce adhesions: autologous, heterologous and synthetic membranes have been used to substitute the damaged pericardium; anti-inflammatory and antihistaminic agents have been used to reduce excessive inflammatory activity; fibrinolitic agents have been used to try to reduce the fibrin. Only after the appearance of the polymer barriers, which reduce the contact between the visceral and parietal pericardium, impeding, therefore, the formation of adhesive bands, is that the results became more consistent and reproducible.

Objectively, all methods try to reduce, one way or another, the quantity of fibrin adhesive bands in 5 to 7 days, when the damaged areas will already be covered by new mesothelial cells.

With the actual advance of cell and molecular biology, it has been possible to control cell development and reproduction by using cytokine like never before. In 1996, it was demonstrated that it is possible to modify the proliferation speed of mesothelial cells. This possibility has not yet been used to try to reconstitute the pericardium membrane's morfo-functional integrity faster, by recovering its fibrinolytic capacity sooner and possibly reducing the intensity of the postoperative adhesions, as well.

Some growth factors have brought considerable increase in the proliferation of mesothelial cells: the keratinocyte growth factor (KGF) and the hepatocyte growth factor (HGF). It is possible that three other factors may share this property, as well: the epidermal growth factor (EGF), the fibroblast growth factor 10 (FGF-10) and the basic fibroblast growth factor (FGF-2).

Based on these considerations arises the hypothesis of using these growth factors as pericardium adhesions reducing agents.

However, the results from previous studies suggest that any method used will only reach its best effectivity if the contact between the damaged surfaces is impeded while they are still mesothelial cells free. In order to do that, an appropriate barrier must be interposed.

Many methods have been tested as postoperative adhesions reducing agents. Among the substitutes, there are the synthetic polymers. The polytetrafluorethylene (PTFE) has been clinically used as a pericardial substitute, but the results were disappointing. In 2002, Ozeren [Ozeren, M., U. Han, et al. (2002), "Consequences of PTFE membrane used for prevention of re-entry injuries in rheumatic valve disease" Cardiovasc Surg 10(5): 489-93] published a series of 7 redo surgeries where the patients had made use of PTFE membrane to close the pericardium, making evident the formation of an intense fibrous membrane that obscured the epicardium and made the dissection of the heart more difficult. In this same publication, the author reports an incidence of accidents of approximately 50%.

In 2005, a group from the Kyushu Unversity [Kajihara, N., M. Eto, et al. (2005), "Three-layered synthetic pericardial substitutes reduce postoperative pericardial adhesions." J Thorac Cardiovasc Surg 129(1): 18-24], tested in animals, a three layered synthetic membrane: one internal polyester membrane interposed between two external silicone-urethane membranes.

This membrane presented better results, smaller adhesion level than the PTFE membrane used for control.

The silicone has also been used in attempt to reduce the deposition of proteins and platelets, Amanpour [Amanpour, S., H. Ahamadi, et al. (2005). "Long-term evaluation of laser-treated silicone (LTS) membrane as a pericardial substitute: in vivo study." J Long Term Eff Med Implants 15(4): 347-54] applied a CO2 laser treatment to the silicone trying to reduce the superficial tension. This experimental study was concluded in 2004, but there are not any reports about its clinical applications up to now. The biggest question regarding this barrier method is its big tendency to have infections related to the use of nonabsorbable materials.

Many biopolymers have been tested to prevent pericardial adhesions. These biomolecules are made up of chemical molecules synthesized by living units and participate in the structure and functioning of the cells. Most of them are organic compounds; its mass is constituted of 97% of carbon, hydrogen, oxygen and nitrogen. In other words, the proteins, glicides and DNA are considered biopolymers.

Theoretically, the ideal biopolymer to use in the prevention of pericardial adhesions must have biochemical characteristics that will allow it to be biocompatible, bioabsorbable and non-toxic. Other important details are its abundancy in nature, easiness to be extracted and preserved, and must be able to be retained in the cavity for at least 5 days.

In this way, Robison [Robison, R. J., J. W. Brown, et al. (1984). "Prevention of pericardial adhesions with dextran 70". Ann Thorac Surg 37(6): 488-90] tested Dextran 70, which is a high molecular mass polysaccharide and that has among its properties the inhibition of platelet aggregation. After this experimental study, no other clinical study using this substance in the pericardium has been published. In 2007, the Cochrane Library [Metwally, M., A. Watson, et al. (2006). "Fluid and pharmacological agents for adhesion prevention after gynaecological surgery". Cochrane Database Syst Rev (2):CD001298.] published a systematic review saying that it did not find evidences of benefits in the use of Dextran 70 in the peritoneal adhesions prevention.

Duncan [Duncan, D. A., Y. Yaacobi, et al. (1988). "Prevention of postoperative pericardial adhesions with hydrophilic polymer solutions". J Surg Res 45(1): 44-9.] described a significant reduction in the severity of adhesions by using another hydrophilic polymer, the polyvinylpyrrolidone. However, the author questioned himself about the long-term effects of this substance when used through parentereal ways. New studies have not been published after this one in order to define better this last aspect or to corroborate the reported results.

A polyethyleneglycol based hydrogel, used primarily as vascular sealant for anastomosis, and that is reabsorbed in approximately 4 weeks, was used by Bennet [Bennett, S. L., D. A. Melanson, et al. (2003). "Next-generation hydrogel films as tissue sealants and adhesion barriers". J Card Surg 18(6):494-9] in animals to observe the pericardial adhesions reductions. This study explored exactly the concept of temporary mechanical separation between the visceral and parietal pericardium created by the interposition of a biodegradable polymer, and found a statistically significant reduction in the adhesions incidence. Marc Hendrikx [Marc Hendrikx, M., U. Mees, et al. (2001). "Evaluation of a novel synthetic sealant for inhibition of cardiac adhesions and clinical experience in cardiac surgery procedures." Heart Surg Forum 4(3): 204-9; discussion 210.] evaluated experimentally the use of the CoSeal®, which is a pharmaceutical composition composed of two polymers of polyethyleneglycol in the pericardial cavity, and found significant differences between the treatment group and the control group. Clinically, there are still no conclusive evidences about its use in the prevention of postoperative adhesions.

The carboxymethylcellulose, a hydrosoluble by product of cellulosis, and the sodium hyaluronate, a human constitutional glicosamine, have been tested by Seeger in animals [Seeger, J. M., L. D. Kaelin, et al. (1997). "Prevention of postoperative pericardial adhesions using tissue-protective solutions." J Surg Res 68(1): 63-6]. Seeger reported better results with the use of hyaluronate than with carboxymethylcellulose. However, the latter presented better results than the control group. The inconvenience of using hyaluronic acid is the difficulty to obtain it, and consequently its cost.

By Mitchell [Mitchell, J. D., R. Lee, et al. (1994). "Prevention of postoperative pericardial adhesions with a hyaluronic acid coating solution. Experimental safety and efficacy studies." J Thorac Cardiovasc Surg 107(6): 1481-8; and Mitchell, J. D., R. Lee, et al. (1994). "Reduction in experimental pericardial adhesions using a hyaluronic acid bioabsorbable membrane." Eur J Cardiothorac Surg 8(3): 149-52.], in these two experimental assays, it was demonstrated the efficacy of hyaluronic acid in pericardial adhesions reduction.

Some biopolymers like polylactide have been tested in a sheet form. In 2006, Tsukihara [Tsukihara, H., S. Takamoto, et al. (2006). "Prevention of postoperative pericardial adhesions with a novel regenerative collagen sheet." Ann Thorac Surg 81(2): 650-7] used a membrane composed of three layers (collagen+hyaluronic acid) and evidenced a reduction in adhesions. However, the author did not follow the adhesions induction protocol commonly used in medical literature. In doing so, the author made it more difficult to compare these results with the ones already published.

Now, the new studies are trying to identify which biopolymer is more effective and in which physical-chemical state it must be used, in addition to evaluating combined therapeutical methods.

There are no doubts that biopolymers are, contemporarily, the first-line agents for postoperative adhesions prevention. The carboxymethylchitosan, a hydrosoluble biopolymer has countless characteristics that are useful in the biomedical area like: being bioabsorbable, nontoxic, having low immunogenicity, being apyretic, and a germicide. But, one aspect that becomes relevant is the sterilization of the carboxymethylchitosan to be used in human beings. Krause [Krause, T. J., G. Zazanis, et al. (2001). "Prevention of pericardial adhesions with N—O carboxymethylchitosan in the rabbit model." J Invest Surg 14(2): 93-7], in 2001, described for the first time the use of this chitosan derivative in pericardial adhesions prevention, but did not describe if the substance was sterilized.

Due to its high molar mass and for being characterized as a hydrodispersible polymer, the chitosan and its derivatives have been broadly used in association with other pharmaceuticals for their sustainable and prolonged absorption. This effect has also been evidenced with macromolecules like the L-Asparaginase enzyme that is used in the acute lymphoblastic leukemia treatment. Recently, some articles reported similar effect in some members of the growth factor family linked to the heparin—heparin-binding growth factors (HBGF), suggesting that there may be positive effects in the association of these growth factors with the chitosan or other glycosaminoglycans.

One of the members of the HBGF family is the keratinocyte growth factor (KGF), also known as fibroblast growth factor-7 (FGF-7). Originally, it was identified in pulmonary fibroblast cultures and its gene transcription generated a polypeptide chain of 24 kilodaltons containing 194 amino acids.

The KGF is known for its effect on ectodermic tissue cells like the epidermis, the mammary glands, the endometrium, the respiratory and gastrointestinal epithelium, the seminal vesicle and the prostate. The KGF/FGF-7 has also proved to be effective in the increase of mesothelial proliferation.

Some studies suggest that the use of KGF may be done in a crossing way between species. In the study done by Adamson [Adamson, I. Y., J. Bakowska, et al. (2000). "Proliferation of rat pleural mesothelial cells in response to hepatocyte and keratinocyte growth factors." Am J Respir Cell Mol Biol 23(3): 345-9], done with rats, the author did not describe from which kind of species the KGF is derived from, but because of the substance's origin one can infer that it was either a human or bovine recombinant factor, since R&D Systems, the substance supplier, only commercializes keratinocyte growth factors of these two species. The existence of another study that shows the activity of human r-KGF in pigs reaffirms the crossing activity of this factor between different species of mammals.

The KGF's instability is another subject that has been studied. This instability is shared with other growth factors of this family, heparin-binding growth factors, like the basic fibroblast growth factor (FGF-2). The heparin has showed to be important for the FGF-2 stabilization. It has been described that this effect is due to the neutralization of segments with positive charges inside the HBGFs peptide chain. Masuoka [Masuoka, K., M. Ishihara, et al. (2005). "The interaction of chitosan with fibroblast growth factor-2 and its protection from inactivation." Biomaterials 26(16): 3277-84] demonstrated that chitosan also has the capacity to stabilize the FGF-2 and reduce its degradation. This stabilizing function seems to be connected to the similarity of the primary structure of heparin and chitosan.

However, pericardial adhesions prevention is still needed in surgical practice. As it is frequently noticed in the discussion about the state of the art in this study, there are many attempts regarding adhesions prevention, nonetheless, these attempts present practical and/or economical limitations.

INVENTION SUMMARY

The main goal of this invention refers to the use of a composition containing a growth factor, which is effective to promote proliferation of mesothelial cells, and also a sterile carboxymethylchitosan for inhibition of postoperative adhesions.

Another goal of this present invention refers to a method to inhibit severity of postoperative adhesions using the composition of the invention.

An additional goal of this present invention refers to the isolated use of growth factors for postoperative adhesions inhibitions.

In this present invention a sterile carboxymethylchitosan (CMQ) is used as a barrier method to be the combined with a modulating factor of mesothelial proliferation, in order to enhance and stabilize the growth factor that is a component in the invention.

The CMQ has the advantages of being biodegradable, nontoxic, hydrosoluble in physiological pH, germicide and of having a high molar mass, which enables it to remain in situ for a period of 4 to 7 days and be degraded through the hydrolytic action of lysozime, which does not cause inflammatory reaction during the process.

A BRIEF DESCRIPTION OF THE FIGURES

DETAILED DESCRIPTION OF THE INVENTION

Figure 1:
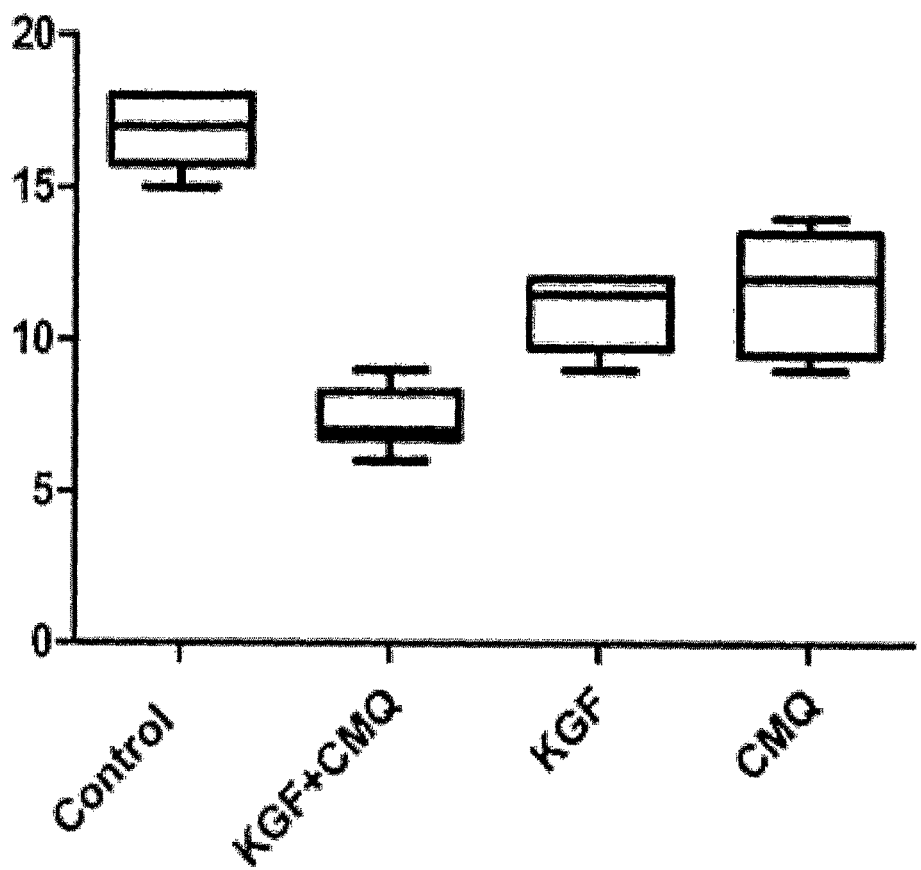
FIG. 1 shows the magnitude of adhesions reduction in each group.

Based on a state-of-the-art exam, the inventors found out that growth factors targeted to the proliferation of mesothelial cells may reduce the severity of postoperative adhesions. Another data that corroborates the studies done by the inventors is that it was verified that the association of carboxymethylchitosan with the KGF enhances the results, demonstrating that the carboxymethylchitosan was effective in stabilizing and enhancing the KGF.

It is important to point out that the carboxymethylchitosan used in this invention underwent a sterilization process that did not affect its physical-chemical characteristics.

Best Way of Realizing the Invention

In the evaluation of the methods, 24 male orquiectomized large-white pigs weighing between 15 and 20 Kg were used.

The animals were treated and operated on in accordance with the Ethical Principles and Guidelines for Experiments on Animals established by the Colégio Brasileiro de Experimentação Animal (The Brazilian College for Experiments on Animals) and the concepts of the *NIH Guide for Care and Use of Laboratory Animals*, which was published in 1996.

The animals were allocated in treatment groups through stratified randomization generated by the public program SISA (Simple Interactive Statistical Analysis) obtained from the site http://home.clara.net/sisa/order.htm.

The carboxymethylchitosan, the KGF human recombinant, the 0.9% sterile sodium chloride and the sterile bidistilled water were used to compose the solutions tested in the animal experimental groups.

Other growth factors like the EGF, the HGF, the FGF-10 and the FGF-2 can be used as alternatives to the recombinant human KGF. The EGF growth factor is used at a concentration of 5 ng/ml to 1 mcg/ml, preferably from about 10 ng/ml to 500 ng/ml, more preferably from about 15 ng/ml to 100 ng/ml and even more preferably from 20 ng/ml to 50 ng/ml. The HGF is used at a concentration of 5 ng/ml to 1 mcg/ml, preferably from about 10 ng/ml to 500 ng/ml, more preferably from about 15 ng/ml to 100 ng/ml and even more preferably from 20 ng/ml a 50 ng/ml. The FGF is used at a concentration of 5 ng/ml to 1 mcg/ml, preferably from about 10 ng/ml to 500 ng/ml, more preferably from about 15 ng/ml to 100 ng/ml and even more preferably from 20 ng/ml to 50 ng/ml. As for the FGF-2, it is used at a concentration of 5 ng/ml to 1 mcg/ml, preferably from about 10 ng/ml to 500 ng/ml, more preferably from about 15 ng/ml to 100 ng/ml and even more preferably from 20 ng/ml to 50 ng/ml.

The carboxymethylchitosan powder (CMQ), was subjected to autoclave sterilization. In the sterilization process of the CMQ, it is used a pre-vacuum lasting about 1 to 30 minutes, preferably lasting from 5 to 6 minutes. The heating time of the CMQ until it reaches the sterilization temperature of 134° C. ranges from 1 minute to 2 hours, preferably from 5 to 30 minutes, and more preferably from 9 to 10 minutes.

After the pre-vacuum application, the sterilization process continued with humid heat for about 1 to 30 minutes, preferably for 25 minutes, more preferably for about 10 to 20 minutes and even more preferably for about 15 to 16 minutes. The pressure used was from 1 to 10 kgf/cm2, preferably from 1.5 to 5 kgf/cm2, and more preferably 2.1 kgf/cm2. The drying done with dry heat occurred from 1 to 2 hours, preferably from 5 minutes to 1 hour, more preferably from 7 minutes to 30 minutes, even more preferably for 10 to 11 minutes.

A carboxymethylchitosan solution from 0.5 to 10%, preferably from 1 to 5%, more preferably from 2 to 4.5% and even more preferably from 3 to 4% was prepared through dilution of sterile carboxymethylchitosan in sterile bidistilled water. This solution was kept in a rotational agitator, at the temperature of 25° C. for 24 hours to be used later in gel form.

The sterilized and nonsterilized carboxymethylchitosan, was subjected to physical-chemical analyses through the measurement of the hydrogenic potential, thermogravimetric analyses, ($^1H$ NMR) hydrogen nuclear magnetic resonance spectroscopy and through infrared spectroscopy.

The processes of physical-chemical analyses were done according to the methods described in the studies done by Campana-Filho e cols [Santos, J. E. d., J. d. P. Soares, et al. (2003)5. "Caracterização de quitosánas comerciais de diferentes origens. "Polímeros 13: 242-249; e, Abreu, F. R. D. and S. P. Campana-Filho (2005)." Preparation and characterization of carboxymethylchitosan." Polímeros 15: 79-83.].

The solutions used in the assay were prepared according to the groups. In the control group, it was used NaCl at 0.9%. In the KGF+CMQ group, the amount of KGF to be used was brought up to ambient temperature and diluted in the sterile hydrated carboxymethylchitosan solution from 0.5 to 10%, preferably from 1 to 5%, more preferably from 2 to 4.5% and even more preferably from 3 to 4%, creating a new solution containing from 5 ng/ml to 1 mcg/ml, preferably from 10 ng/ml to 500 ng/ml, more preferably from 15 ng/ml to 100 ng/ml, and even more preferably from 20 ng/ml to 50 ng/ml of KGF+sterile hydrated carboxymethylchitosan from 0.5 to 10%, preferably from 2 to 4.5% and even more preferably from 3 to 4% (KGF+CMQ). In the KGF group, the amount of KGF to be used was brought up to ambient temperature and diluted in bidistilled water, creating a new solution containing from 5 ng/ml to 1 mcg/ml, preferably from 10 ng/ml to 500 ng/ml, more preferably from 15 ng/ml to 100 ng/ml, even more preferably from 20 ng/ml to 50 ng/ml of KGF. In the CMQ group, it was used a solution containing sterile hydrated carboxymethylchitosan from 0.5 to 10%, preferably from 1 to 5%, more preferably from 2 to 4.5% and even more preferably from 3 to 4%.

As an alternative to the carboxymethylchitosan solution, the growth factors can be ionically or nonionically absorbed or crosslinked with chitosan-polymer membranes, carboxymethylchitosan, trimethylchitosan, hyaluronic acid or sodium hyaluronate associated with carboxymethylcellulose, regenerated forms of oxidated cellulose, and decellularized collagen.

Regarding the animal experimentation, the pigs were anesthetized and subjected to a right anterolateral thoracotomy. For the pericardial adhesions induction, it was used a model made up of mechanical abrasion, autologous blood instillation and drying. After closing the pericardium, the solutions prepared, as described above, were administered, according to the randomization plan, in the pericardial cavity through a catheter inserted via another incision. The catheter was removed after the solutions were administered and its opening was stitched in a way that there was no significant escape of the solution administered. The surgery was finished after closing the chest wall.

The animals were sacrificed 8 weeks after the experiment. The existing adhesions were classified according to its importance through criteria that have already been used by other authors as it is shown in table 1.

TABLE 1

| Adhesions Classification System | |
|---|---|
| Adhesions scoring | Characteristics |
| I | Loose adhesions, easily undone with finger dissection, presenting a foamy appearance between surfaces and bloodless. |
| II | Intermediate adhesions that are undone with a more aggressive dissection or with the use of few sharp dissection, presenting an identifiable plan between surfaces, which results in moderate bleeding. |
| III | Firm adhesions that are only undone with sharp dissection, without a well defined plan between surfaces, which bleed easily. |

TABLE 1-continued

The areas for macroscopic analyses were the following: (I) right ventricle and left ventricle anterior face, (II) left ventricle lateral face, (III) right ventricle and left ventricle inferior face, (IV) pericardium closing line, (V) inferior suture of the atrium and (VI) the suture of the aorta. The analysis of part of these areas was used to establish a severity score called total score.

For each animal, the total score was calculated by adding up the adhesion degree found in each of the areas mentioned in the previous paragraph. The total score was used as one of the variables to compare the adhesions severity among the animals. The time spent from the opening of the pericardium until the end of the adhesiolysis was measured using a digital chronometer. Two video recording cameras were used to film the procedure for subsequent quantification of the absolute number of times it was necessary to use a sharp instrument in the adhesiolysis.

After the heart explantation, it was done a biopsy of an area where the adhesions were not lysed, which was located between the suture of the inferior part of the atrium and the suture in the atrial appendix. The structures of this biopsy represent from the exterior to the interior, the parietal pericardium, adhesions and the right atrium. This fragment was fixed in buffered formalin solution at 10% for 48 hours.

After the usual histological processing, blocks of paraffin containing the biopsy fragment were made. Thereafter, 5 μ thick sections were cut and stained with Sirius red.

The Sirius red was used for the semiquantitative morphometrical analysis. The histological sections were evaluated through optical microscopy; it was used 5× objective lens. The images were digitalized using a digital video camera (JVC KY-F55B, JAPAN) with a 768×576 pixels resolution (vertical×horizontal) connected to the microscope. The size of the pixel was converted into micrometers and the analysis of the images was done using a computer program (Quantimet-Leica, Leica Cambridge Ltd., Cambridge, United Kingdom). The statistical analysis was done in a descriptive and comparative way. The categorical variables were expressed through the mediana, minimum and maximum values. The average and the standard deviation were calculated for the continuous variables. In order to test the homogeneity of the groups in relation to the categorical variables, the Kruskal-Wallis test was used for testing independent variables.

The Dunn test for multiple comparisons was used after the Kruskal-Wallis test.

In order to compare the four groups in relation to the quantitative variables, it was used the one-way ANOVA test for variance analysis and later the Bonferroni test was used for multiple comparisons. It was established the determination coefficient ($r^2$) to analyze the correlation between the total score and the adhesions dissection time and between the total score and the amount of sharp dissection used in the lyses of the adhesions. All tests were done using the Graph-Pad Prism computer program, version 5.01. An alpha error (type 1) of 5% was set as a limit for statistical significance.

In the macroscopic analysis of the adhesions intensity, based on the specifications of table 1, a significant difference was shown between the scores of the groups for all areas (Kruskal-Wallis, p=0.01). The magnitude of the adhesions reduction in each group, described through the total score on table 2, is shown in FIG. 1.

TABLE 2

Cumulative evaluation of adhesions in the segments of macroscopic analysis (total score)

| | | CONTROL | KGF + CMQ | KGF | CMQ |
|---|---|---|---|---|---|
| Total score | Mediana | 17.0 | 7.0 | 11.5 | 12.0 |
| | Maximum | 18.0 | 9.0 | 12.0 | 14.0 |
| | Minimum | 15.0 | 6.0 | 9.0 | 9.0 |

Data presented in mediana (max.-min.)
p = 0.0003 - Kruskall-Wallis test

When compared to the control group, the association KGF+CMQ, revealed to be highly significant (p<0.01) (Table 3) in reducing the adhesions score.

TABLE 3

Multiple comparative analyses between the groups based on the total score.

| | CONTROL | KGF + CMQ | KGF | CMQ |
|---|---|---|---|---|
| control | — | p < 0.01 | p < 0.05 | NS |
| KGF + CMQ | p < 0.01 | — | p < 0.01 | p < 0.01 |
| KGF | p < 0.05 | p < 0.01 | — | NS |
| CMQ | NS | p < 0.01 | NS | — |

The Dunn test
NS—No statistical significance

Surprisingly, the inventors proved that the KGF also showed to be effective (0.01<p<0.05) when used separately. The CMQ did not reach statistical significance level when used separately. In the comparison of the KGF+CMQ solution with the KGF used separately and the CMQ separately, it is possible to notice a significant statistical difference (p<0.01), suggesting an additive effect of the two substances, which shows the association's synergy.

In order to compare the adhesions intensity in the anterior wall and the aorta's suture, it was used the Dunn test for multiple comparisons after applying the Kruskal-Wallis test. In the anterior wall and the aorta's suture, in comparison to the control group, the combination KGF+CMQ showed to be effective in adhesions reduction (p<0.01), as well as the KGF used separately (0.01<p<0.05). There were not any significant statistical differences between the control group versus CMQ, the KGF+CMQ versus the KGF or CMQ groups and between KGF versus CMQ, as it is shown in table 4.

TABLE 4

Adhesions macroscopic classification

| Group | Anterior Face | Lateral Face | Inferior Face | Suture line | Atrium's suture | Aorta's suture |
|---|---|---|---|---|---|---|
| Control | 3.0 (2-3) | 2.0 (2-3) | 3.0 (2-3) | 3.0 (3-3) | 3.0 (3-3) | 3.0 (2-3) |
| KGF + CMQ | 1.0 (1-2)** | 1.0 (1-1)* | 1.0 (1-1)* | 2.0 (1-2)** | 1.0 (1-1)* | 2.0 (1-2)** |
| KGF | 1.5 (1-2)*** | 1.5 (0-2)*** | 2.0 (1-2) | 3.0 (2-3) | 2.0 (2-3) | 2.0 (1-2)*** |
| CMQ | 2.0 (1-2) | 1.0 (1-2) | 2.0 (1-2) | 3.0 (2-3)† | 2.0 (1-3) | 2.0 (1-2) |

Data presented in mediana (max.-min.)
p < 0.01 - Kruskal-Wallis test
Dunn test:
*p < 0.001 versus control group;
**p < 0.01 versus control group;
***p < 0.05 versus control group
†p < 0.05 versus KGF + CMQ In the lateral wall, in relation to the control group, the combination KGF+CMQ showed to be very effective in adhesions reduction (p<0.001). The same happened with the KGF and the CMQ when used separately, but with less intensity (0.01<p<0.05). In this wall, some differences were found when comparing the KGF+CMQ versus The CMQ (0.01<p<0.05). There were not any significant statistical differences between the KGF+CMQ versus the KGF and between the KGF versus the CMQ (Table 4).

In the inferior wall and in the right atrium's suture, the association KGF+CMQ was highly significant in reducing adhesions in relation to the control group (P<0.001). The use of the KGF and the CMQ separately was not significant in relation to the control group. There were not any significant statistical differences between the KGF+CMQ versus the KGF or between the KGF versus the CMQ (Table 4).

In the closing line of the pericardium, the association KGF+CMQ reduced adhesions in this area significantly (p<0.01) in relation to the control group, the same did not happen when the KGF and CMQ were used separately. It was evidenced a difference between the KGF+CMQ groups versus CMQ (0.01<p<0.05). There were not any significant statistical differences between the KGF+CMQ versus the KGF and between the KGF versus the CMQ (Table 4).

Figure 2:
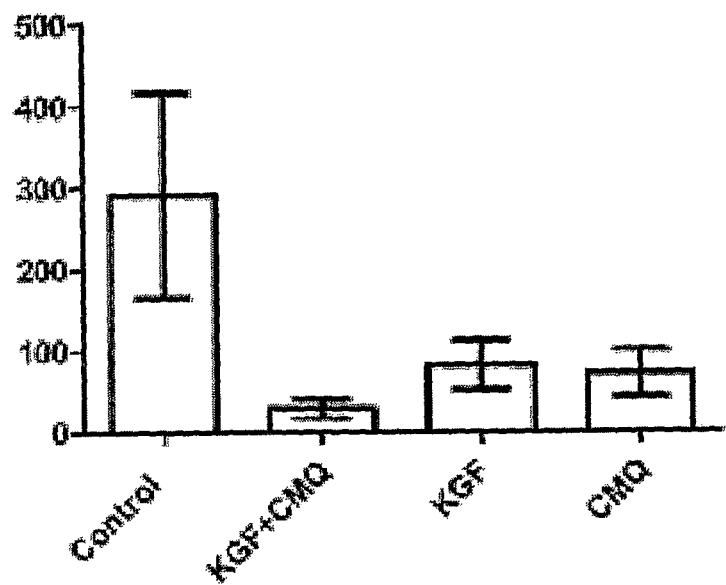
FIG. 2 shows the quantitative evaluation of the use of sharp dissection.

In relation to the quantitative evaluation of the use of sharp dissection, the number of cutting dissecting movements needed to have adhesions lyses was 292±101, 29±11, 82±28, 72±23 for the control groups, KGF+CMQ, KGF and CMQ respectively. A significant difference (p<0.0001) between the groups was found through the one-way ANOVA analysis of variance. The Bonferroni multiple comparison test was used in order to identify the groups involved. In relation to the control group, this evaluation revealed that all treatment groups reduced significantly (p<0.001) the amount of sharp dissection. There were not any significant statistical differences between the KGF+CMQ versus the KGF groups or between the KGF versus the CMQ, as it is shown in FIG. 2.

Figure 3:
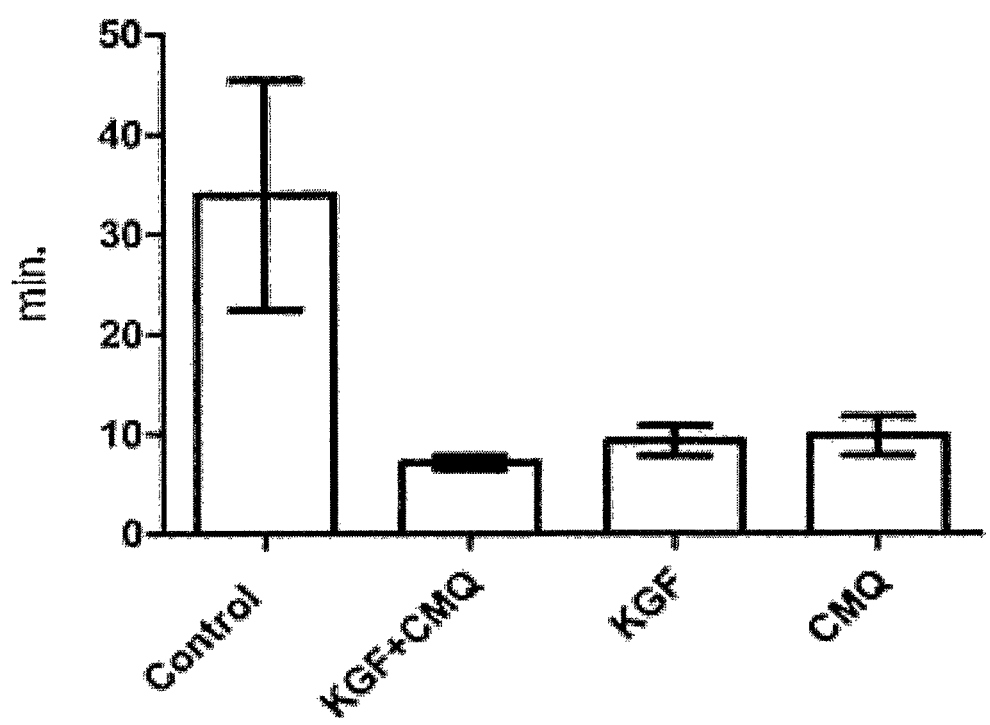
FIG. 3 shows the analysis of the adhesions dissection time.
Figure 4:
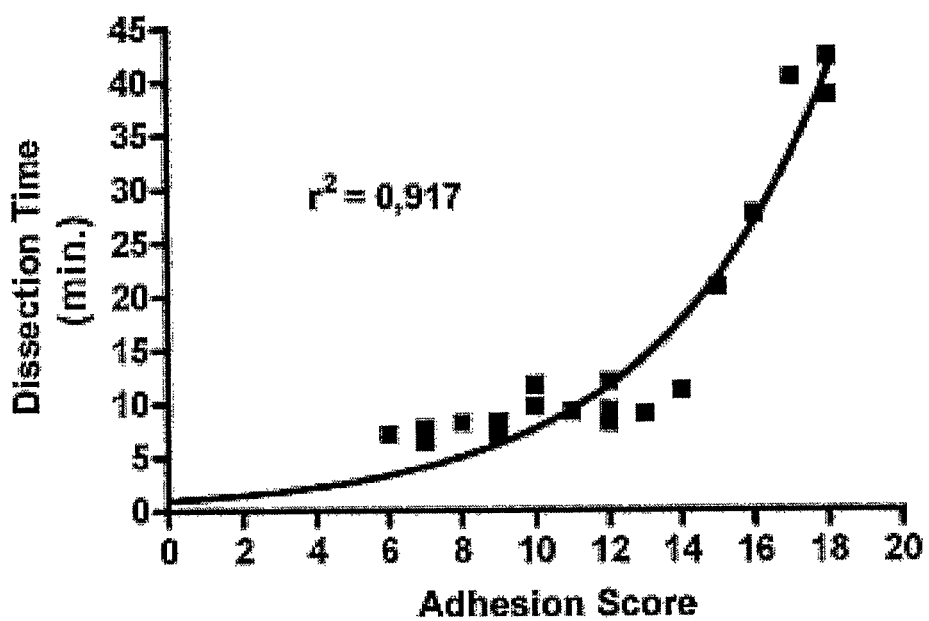
FIG. 4 shows the correlation between the total score and the dissection time.

In the evaluation of the amount of dissection time to open the pericardium and to adhesions lyses, the average±standard deviation was calculated. They were 33.9±9.2 min for the control group, 7.1±0.6 min for the KGF+CMQ, 9.2±1.4 min for the KGF group and 9.8±1.5 min for the CMQ group, as it is shown in FIG. 3.

The one-way ANOVA variance analysis of this variable evidenced a significant difference (p<0.0001) between the groups. The Bonferroni multiple comparison test was used in order to identify the groups involved.

This analysis evidenced a significant reduction (p<0.001) regarding the dissection time in relation to the control group in all three treatment groups. There were not any statistical significant differences between the KGF+CMQ versus the KGF or CMQ groups and between the KGF versus the CMQ, as it is shown in FIG. 3.

The digital morphometrical analysis of the histological sections (Tables 5, 6, 7) showed that the combination KGF+CMQ reduced the area of the parietal pericardium, as well as the area of the adhesions and the epicardium.

TABLE 5

Morphometrical measurements of the parietal pericardium obtained through the image analyzer (QUANTIMET). Sirius Red stain (5x)

| Group | Area of the pericardium § † | Area of collagen in the pericardium § † | % of collagen in the pericardium |
|---|---|---|---|
| Control | 60.9 (±26.1) | 58.2 (±2.4) | 96.1 (±2.0) |
| KGF + CMQ | 26.6 (±5.9) * | 24.8 (±5.6) * | 93.0 (±5.0) |
| KGF | 26.0 (±3.8) * | 25.1 (±3.2) * | 96.6 (±2.7) |
| CMQ | 45.6 (±10.8) | 43.5 (±10.7) | 95.2 (±3.5) |

All values are average ± standard deviation and are expressed in μ.
One-way ANOVA:
† p = 0.001;
The Dunn Test:
* p < 0.05 versus control group;
§ value × $10_{-4}$

TABLE 6

Morphometrical measurements of adhesions obtained through the image analyzer (QUANTIMET). Sirius Red stain (5x).

| Group | Adhesions area § † | Area of collagen in adhesions § $ | % of collagen in adhesions # |
|---|---|---|---|
| Control | 61.7 (2 ± 5.9) | 26.2 (±15.3) | 41.8 (±10.4) |
| KGF + CMQ | 31.9 (±9.8) * | 6.7 (±2.2) * | 21.8 (±6.7) * |
| KGF | 26.2 (±13.2) * | 9.9 (±5.9) * | 36.3 (±5.5) |
| CMQ | 44.1 (±12.9) | 15.9 (±6.8) | 37.4 (±14.2) |

All values are average ± standard deviation and are expressed in μ.
One-way ANOVA:
# p = 0.01;
† p = 0.008;
$ p = 0.007;
The Dunn Test:
* p < 0.05 versus control group;
§ value × $10_{-4}$

TABLE 7

Morphometrical measurements of the epicardium obtained through the image analyzer (QUANTIMET). Sirius red stain (5x)

| Group | Epicardium's area § † | Area of collagen in the epicardium § # | % of collagen in the epicardium |
|---|---|---|---|
| Control | 65.2 (±25.7) | 44.0 (±22.2) | 66.4 (±13.7) |
| KGF + CMQ | 24.3 (±15.9) * | 16.4 (±13.6) * | 68.2 (±27.7) |
| KGF | 23.8 (±13.7) * | 17.8 (±10.5) * | 74.3 (±7.0) |
| CMQ | 29.6 (±18.3) * | 18.9 (±11.7) | 64.0 (±21.9) |

All values are average ± standard deviation and are expressed in μ.
One-way ANOVA:
# p = 0.01;
† p = 0.003
The Dunn Test:
* p < 0.05 versus control group
§ value × $10_{-4}$ The amount of collagen in the parietal pericardium, in the adhesion and in the epicardium also presented itself less intense in this group. The proportion of collagen in the adhesion was also smaller in the animals that received KGF+CMQ.

In the group that received the only KGF it was possible to notice a reduction of area in the parietal pericardium, in the adhesion and in the epicardium. In this same group, the amount of collagen in all segments analyzed was smaller.

When used separately, the CMQ reduced the area of the epicardium in a statistically significant way.

Figure 5A:
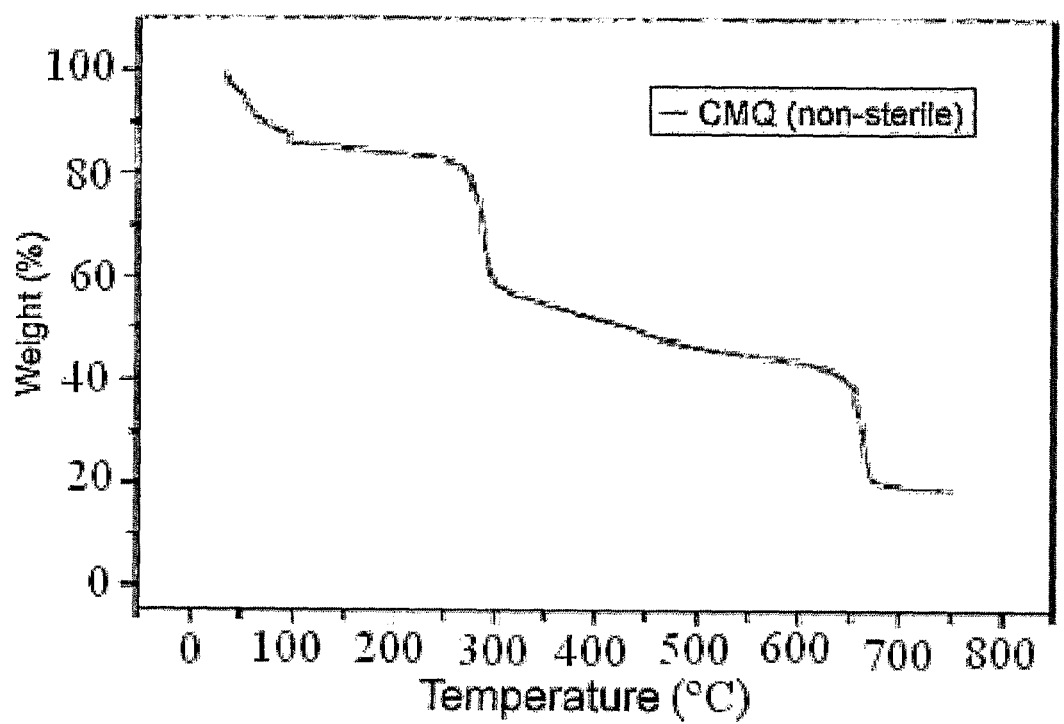
FIGS. 5A, 5B and 5C show the thermogravimetric analysis.
Figure 5B:
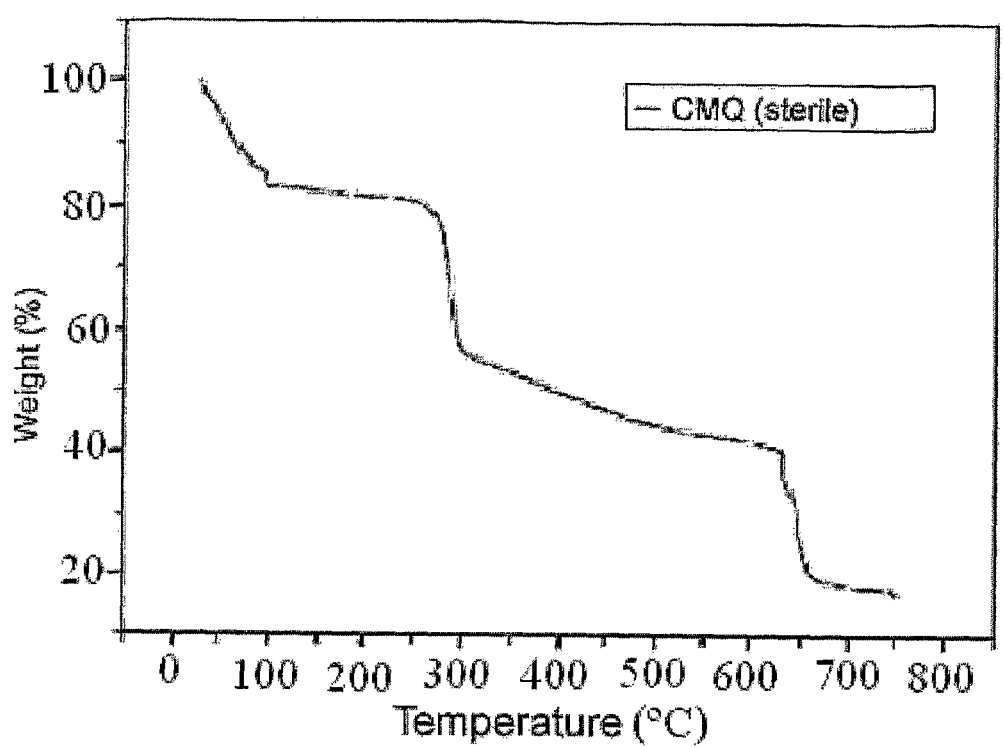
Figure 5C:
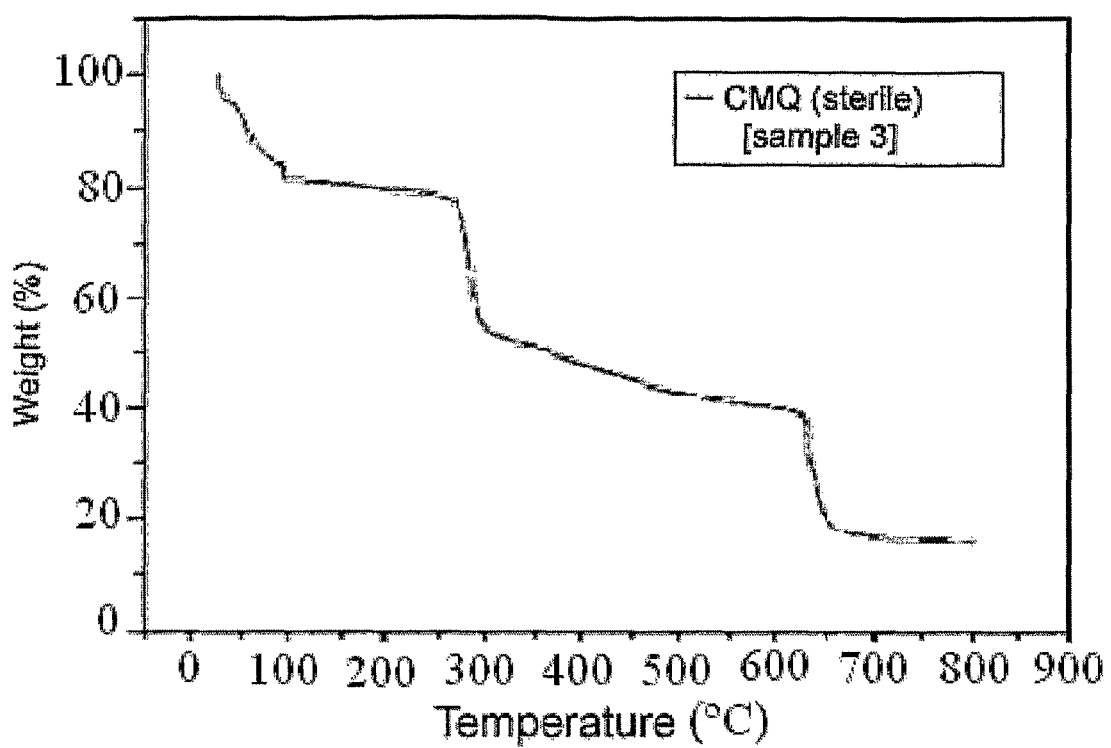

In the physical-chemical analysis of the carboxymethylchitosan, the pH measurements were done after magnetic agitation of the CMQ at 4% for 3 days at ambient temperature from about 20 to 25° C. After this agitation period, it was noticed that the nonsterilized solution (CMQNEst) presented a yellow color and the sterilized solution (CMQEst) presented a light brown color. It was used the pH meter to take measurements. The results did not differ in the samples, the pH being equal to 8.9. In relation to the thermogravimetric analysis, the values are shown in table 8 and the resulting curves are shown in FIGS. 5A, 5B and 5C.

TABLE 8

Mass variation of the sample in function of the temperature.

| | Temperature (° C.) | | | |
|---|---|---|---|---|
| | 25-100 | 100-310 | 310-550 | 550-750 |
| CMQNEst | 13.6 | 27.6 | 12.1 | 25.2 |
| CMQEst | 16.6 | 28.0 | 12.1 | 25.9 |
| CMQESt | 16.6 | 28.4 | 14.8 | 25.5 |

The values represent loss of mass (%).

The samples behaved in a very similar way, differing only in their humidity content. The samples that had been subjected to sterilization had higher water content. From this result it is not possible to distinguish the sterilized samples from the nonsterilized regarding decomposition and thermal stability.

Figure 6A:
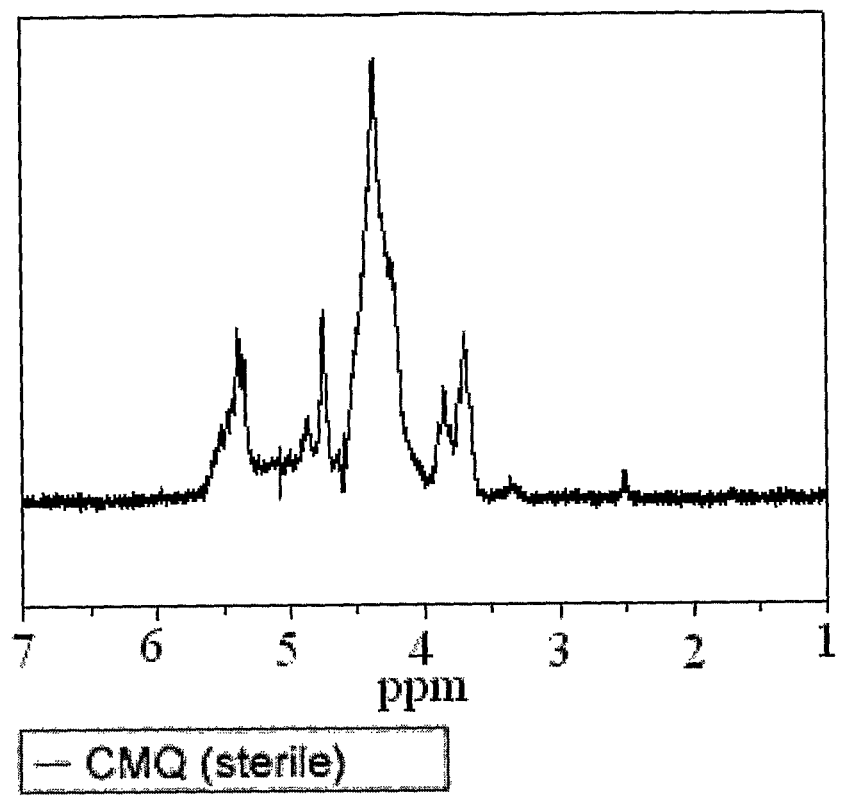
FIGS. 6A and 6B show the results of the hydrogen nuclear magnetic resonance spectroscopy ($^1H$ MNR) of the CMQESt and CMQNEst sample spectra, respectively.
Figure 6B:
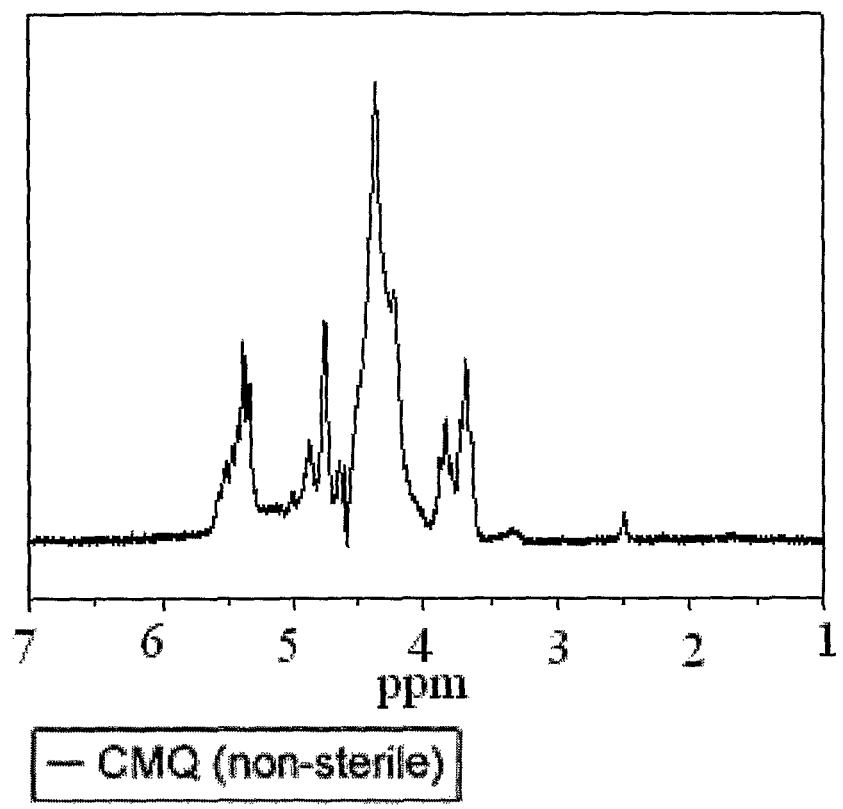

In the hydrogen nuclear magnetic resonance spectroscopy ($^1$H NMR), the comparison of the spectra of the CMQEst and CMQNEst samples do not reveal important differences, as it is shown in FIGS. 6A and 6B. The spectra $^1$H NMR from CMQEst and CMQNEst were captured from the solutions of the samples in $D_2O$/HCl (100/1 v/v) obtained at 80° C.

In FIGS. 6A and 6B, the spectra of the samples also exhibit similarities to the Campana-Filho e cols' samples. Still in the same FIGS. 6A and 6B, in the signal more to the right (≈2.5 ppm) the intensity is very low and must be attributed to the three hydrogen atoms of the methyl of acetamide groups, indicating that the chitosan used to prepare the CMQ samples is considerably desacetylated. Between 3.5 ppm and 4.0 ppm are the signals attributed to the introduction of one or two carboxymethyl groups in the amino radical of chitosan. Due to the introduction of a carboxymethyl group into the chitosan hydroxyls, it appears above 4.0 ppm and superposes itself to other signals, making it more difficult to make identification. Despite that, it is possible to characterize the sample used as the O,N carboxymethylchitosan.

It was also possible to notice, in the infrared spectroscopy that the spectra are very similar among the samples, indicating that the sterilization did not cause important changes in the structure of the samples.

If compared to the samples prepared by Campana-Filho and cols, it can be affirmed that the samples used are in sodium form, which is evidenced by the intense bands located in approximately 1410 cm-1 and 1600 cm-1. In all the spectra there is a very high band in approximately 1100 cm-1 that refers to the glycosidic connections between the polymer's constituting units.

It is important to mention that the carboxymethylchitosan used in the invention could be in a chemical hydrated and sterilized form, or in a liofilized and sterilized chemical form.

Now that the favorite description of the invention has been presented, many advantages of the invention become obvious. Among these advantages, the use of growth factors to inhibit postoperative adhesions like, the KGF, the HGF, the EGF, the FGF-10 and the FGF-2 stand out. As it has been demonstrated, according to this present invention, growth factors can be used separately and in combination with a sterilized carboxymethylchitosan, which enhanced the use of a growth factor to prevent postoperative adhesions.

The application dosage of the composition of the present invention containing a growth factor and a carboxymethylchitosan is preferably in an "acceptable therapeutic quantity", which can be described as being enough to protect the subject. In other words, the application dosage and the time of application depend on the age, weight and the condition of the subject, among other details known to specialists.

It must be understood that the invention's chosen modality here described is presented only as an example of a possible form of the invention. Therefore, variations and modifications can be done in the modality of the invention as described without departing from its spirit and scope, as defined by the claims.

The invention claimed is:

1. A pharmaceutical composition comprising a solution containing a pharmaceutically acceptable amount of carboxymethylchitosan and at least one growth factor selected from a group consisting of keratinocyte growth factor; and fibroblast growth factor-10.

2. The pharmaceutical composition of claim 1 wherein the pharmaceutically acceptable amount of growth factor is from 5 ng/ml to 1 mcg/ml.

3. The pharmaceutical composition of claim 2 wherein the pharmaceutically acceptable amount of growth factor is from 10 ng/ml to 500 ng/ml.

4. The pharmaceutical composition of claim 3 wherein the pharmaceutically acceptable amount of growth factor is from 15 ng/ml to 100 ng/ml.

5. The pharmaceutical composition of claim 4 wherein the pharmaceutically acceptable amount of growth factor is from 20 ng/ml to 50 ng/ml.

6. The pharmaceutical composition of claim 1 wherein the pharmaceutically acceptable amount of carboxymethylchitosan is from 0.5 to 10 wt/vol %.

7. The pharmaceutical composition of claim 6 wherein the pharmaceutically acceptable amount of carboxymethylchitosan is from 1 to 5 wt/vol %.

8. The pharmaceutical composition of claim 7 wherein the pharmaceutically acceptable amount of carboxymethylchitosan is from 2 to 4.5 wt/vol %.

9. The pharmaceutical composition of claim 8 wherein the pharmaceutically acceptable amount of carboxymethylchitosan is from 3 to 4 wt/vol %.

\* \* \* \* \*